US011346831B2

(12) United States Patent
Han et al.

(10) Patent No.: US 11,346,831 B2
(45) Date of Patent: May 31, 2022

(54) INTELLIGENT DETECTION METHOD FOR BIOCHEMICAL OXYGEN DEMAND BASED ON A SELF-ORGANIZING RECURRENT RBF NEURAL NETWORK

(71) Applicant: Beijing University of Technology, Beijing (CN)

(72) Inventors: Honggui Han, Beijing (CN); Yanan Guo, Beijing (CN); Junfei Qiao, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 431 days.

(21) Appl. No.: 15/186,260

(22) Filed: Jun. 17, 2016

(65) Prior Publication Data

US 2017/0185892 A1 Jun. 29, 2017

(30) Foreign Application Priority Data

Dec. 27, 2015 (CN) ........................ 201510999765.5

(51) Int. Cl.
*G01N 33/18* (2006.01)
*G06N 3/04* (2006.01)
(Continued)

(52) U.S. Cl.
CPC ......... *G01N 33/1806* (2013.01); *C02F 3/006* (2013.01); *C02F 3/12* (2013.01);
(Continued)

(58) Field of Classification Search
CPC ........ G05B 19/406; G05B 2219/40585; G06N 3/0445; G06N 3/082; G06N 3/08;
(Continued)

(56) References Cited

U.S. PATENT DOCUMENTS 10,570,024 B2 * 2/2020 Han .................... G06N 3/0445
2014/0052422 A1 * 2/2014 Wan .................... G05B 13/048
703/2

FOREIGN PATENT DOCUMENTS

CN 101957356 * 1/2011
CN 101957356 A * 1/2011
(Continued)

OTHER PUBLICATIONS

Honggui Han, "Nonlinear Model-Predictive Control for Industrial Processes: An Application to Wastewater Treatment Process" Apr. 2014, IEEE Transactions on Industrial Electronics vol. 61 pp. 1970-1982 (Year: 2014).*

(Continued)

*Primary Examiner* — Luis A Sitiriche
*Assistant Examiner* — Chase P. Hinckley
(74) *Attorney, Agent, or Firm* — Leonid Kisselev

(57) ABSTRACT

Under conventional techniques, wastewater treatment has many problems such as poor production conditions, serious random interference, strong nonlinear behavior, large time-varying, and serious lagging. These problems cause difficulty in detecting wastewater treatment parameters such as biochemical oxygen demand (BOD) values that are used to monitor water quality. To solve problems associated with monitoring BOD values in real-time, the present disclosure utilizes a self-organizing recurrent RBF neural network designed for intelligent detecting of BOD values. Implementations of the present disclosure build a computing model of BOD values based on the self-organizing recurrent RBF neural network to achieve real-time and more accurate detection of the BOD values (e.g., a BOD concentration). The implementations herein quickly and accurately obtain BOD concentrations and improve the quality and efficiency of wastewater treatment.

5 Claims, 17 Drawing Sheets

(51) Int. Cl.

| | |
|---|---|
| ***G06N 3/08*** | (2006.01) |
| ***C02F 3/00*** | (2006.01) |
| ***C02F 3/12*** | (2006.01) |
| *G05B 19/406* | (2006.01) |

(52) U.S. Cl.
CPC ............. *G06N 3/0445* (2013.01); *G06N 3/08* (2013.01); *C02F 2209/08* (2013.01); *G05B 19/406* (2013.01); *G06N 3/082* (2013.01)

(58) Field of Classification Search
CPC ....... G06N 3/088; Y02P 80/114; Y04S 10/54; G01N 33/1806; C02F 3/006; C02F 3/12; C02F 2209/08
USPC ............................................................ 706/25
See application file for complete search history.

(56) References Cited

FOREIGN PATENT DOCUMENTS

| | | | |
|---|---|---|---|
| CN | 102073797 | | 5/2011 |
| CN | 102662040 A | * | 9/2012 |
| CN | 103886369 | | 6/2014 |

OTHER PUBLICATIONS

Honggui Han et al., "An efficient self-organizing RBF neural network for water quality prediction" Sep. 2011 Elsevier vol. 24, Issue 7, pp. 717-725 (Year: 2011).*
Bing Li et al., "Research on Optimized RBF Neural Network based on GA for Sewage Treatment" 2013 IEEE Fifth International Conference on Intelligent Human-Machine System and Cybernetics pp. 520-523 (Year: 2013).*
Qi Liu et al., "Neural Network Identification of Wastewater Treatment Plants" Jun. 16-19, 2015 23rd Mediterranean Conference on Control and Automation (MED) pp. 840-846 (Year: 2015).*
Fanjun, Li et al., "A Fast Growing Cascade Neural Network for BOD Estimation" Jul. 28-30, 2015 Proceedings of the 34th Chinese Control Conference pp. 3417-3422 (Year: 2015).*
Vojinovic et al., "Data Assimilation Using Recurrent Radial Basis Function Neural Network Model" Jul. 29-31, 2003, International Symposium on Computation Intelligence for Measurement Systems and Applications, pp. 61-66. (Year: 2003).*
Han et al., "Biological Oxygen Demand (BOD) Soft Measuring based on Dynamic Neural Network (DNN): A Simulation Study" Aug. 27-29, 2009, Proceedings of the 7th Asian Control Conference, pp. 757-762. (Year: 2009).*
Mirbagheri et al., "Performance evaluation and modeling ofa submerged membrane bioreactor treating combined municipal and industrial wastewater using radial basis function neural networks" Mar. 13, 2015, Journal of Environmental Health Science & Engineering, pp. 1-15. (Year: 2015).*
Elnekave et al., "Artificial Neural Network Predictions of Up-Flow Anaerobic Sludge Blanket (UASB) Reactor Performance in the Treatment of Citrus Juice Wastewater" 2012, pp. 49-56. (Year: 2012).*
Li, Xiangfei, "Neural networks modeling of stream nitrogen using remote sensing information: model development and application" Fall 2009, Doctoral Dissertation, University of Alberta, pp. i-195. (Year: 2009).*
Pan et al., "Model Predictive Control of Unknown Nonlinear Dynamical Systems Based on Recurrent Neural Networks" Aug. 2012, IEEE Transactions on Industrial Electronics, vol. 59, No. 8, pp. 3089-3101. (Year: 2012).*
Liu et al., "Neural Network Identification of Wastewater Treatment Plants" Jun. 16-19, 2015, IEEE 23rd Mediterranean Conference on Control and Automation, pp. 840-846. (Year: 2015).*
Patan, Krysztof, "Neural Network-Based Model Predictive Control: Fault Tolerance and Stability" May 2015, IEEE Transactions on Control Systems Technology, vol. 23, No. 3, pp. 1147-1155. (Year: 2015).*
Chen et al., "Modeling of Wastewater Treatment Process Using Recurrent Neural Network" Jul. 6-9, 2010, IEEE Proceedings of the 8th World Congress on Intelligent Control and Automation, pp. 5872-5876. (Year: 2010).*
Li et al., "Research on Optimized RBF Neural Network based on GA for Sewage Treatment" 2013, IEEE Fifth International Conference on Intelligent Human-Machine Systems and Cybernetics, pp. 520-523. (Year: 2013).*
Han et al., "Hierarchical Neural Network Modeling Approach to Predict Sludge Volume Index of Wastewater Treatment Process" Nov. 2013, IEEE Transactions on Control Systems Technology, vol. 21, No. 6, pp. 2423-2431. (Year: 2013).*
Han et al., "A Self-Organizing Fuzzy Neural Network Based on a Growing-and-Pruning Algorithm" Dec. 2010, IEEE Transactions on Fuzzy Systems, vol. 18, No. 6, pp. 1129-1143. (Year: 2010).*
Shim et al., "Recurrent Neural Network for forecasting water quality parameters: Sensitivity Analysis" Jul. 2015, pp. i-15. (Year: 2015).*
"Design of soft measurement instrument for BOD parameters based on neural network," Junfei et al., Computers and Applied Chemistry, Oct. 28, 2013; vol. 30 (Issue 10); pp. 1119-1222, retrieved from https://en.cnki.com.cn/Article_en/CJFDTotal-JSYH201310029.htm.

* cited by examiner

Training samples:

Table 1. The input of chemical oxygen demand (COD) (mg/L)

| | | | | | | | | | |
|---|---|---|---|---|---|---|---|---|---|
| 56.4879 | 47.3704 | 46.9578 | 57.0968 | 23.674 | 87.1841 | 65.4024 | 33.2328 | 45.7022 | 38.8707 |
| 60.4044 | 31.3813 | 61.3711 | 58.7581 | 24.3711 | 44.6108 | 51.2855 | 31.2941 | 26.0306 | 56.3324 |
| 65.5975 | 27.4353 | 15.2992 | 69.9526 | 13.7726 | 95.3596 | 60.5583 | 37.7425 | 45.4243 | 28.9294 |
| 30.3749 | 31.0244 | 61.5002 | 58.3175 | 24.1537 | 45.2169 | 46.5357 | 41.9579 | 25.7405 | 57.0639 |
| 25.7593 | 27.8406 | 15.7437 | 69.6059 | 14.0316 | 95.4633 | 55.2122 | 57.2485 | 25.8236 | 38.675 |
| 40.7136 | 31.666 | 62.1044 | 58.5166 | 24.2027 | 44.4136 | 56.5535 | 32.0409 | 29.1797 | 50.6366 |

FIGURE 6

Training samples:

Table 2. The input of dissolved oxygen concentration (DO) (mg/L)

| 2.4896 | 2.531 | 2.1323 | 2.0047 | 2.0351 | 2.4336 | 1.7658 | 2.1427 | 2.1511 | 2.3133 |
|---|---|---|---|---|---|---|---|---|---|
| 2.0114 | 2.3125 | 2.3339 | 1.718 | 2.2589 | 2.0481 | 2.3616 | 2.4025 | 1.5449 | 2.2669 |
| 2.4997 | 2.5678 | 2.1932 | 2.0142 | 2.0468 | 2.5148 | 1.7352 | 2.2278 | 2.0816 | 2.3706 |
| 1.977 | 2.3401 | 2.3653 | 1.7458 | 2.2664 | 1.9705 | 2.3155 | 2.4314 | 1.5206 | 2.2845 |
| 2.5096 | 2.5754 | 2.2005 | 1.968 | 2.0078 | 2.4422 | 1.7118 | 2.2329 | 2.0777 | 2.3 |
| 2.0414 | 2.3256 | 2.2715 | 1.7084 | 2.2561 | 2.0067 | 2.3229 | 2.4439 | 1.5831 | 2.2151 |

FIGURE 7

Training samples:

Table 3. The input of pH

| 7.0348 | 6.6459 | 7.3787 | 7.9318 | 6.6634 | 5.9972 | 7.2194 | 6.9975 | 7.2398 | 6.0088 |
|---|---|---|---|---|---|---|---|---|---|
| 7.9318 | 6.6634 | 5.9972 | 7.2194 | 6.9975 | 7.2398 | 6.0088 | 7.0112 | 6.9415 | 6.2741 |
| 7.2194 | 6.9975 | 7.2398 | 6.0088 | 7.0112 | 6.9415 | 6.2741 | 7.3441 | 7.1341 | 5.6657 |
| 6.0088 | 7.0112 | 6.9415 | 6.2741 | 7.3441 | 7.1341 | 5.6657 | 5.8402 | 5.4818 | 6.6093 |
| 6.2741 | 7.3441 | 7.1341 | 5.6657 | 5.8402 | 5.4818 | 6.6093 | 6.4104 | 6.8877 | 6.9914 |
| 7.3543 | 7.2689 | 5.5129 | 7.4175 | 7.0246 | 7.2448 | 7.0571 | 7.705 | 6.0055 | 5.9073 |

FIGURE 8

Training samples:

Table 4. The input of suspended solids concentration (SS) (mg/L)

| 35.6622 | 33.5443 | 30.3112 | 43.0785 | 28.3356 | 27.552 | 38.713 | 36.1541 | 32.6892 | 34.2482 |
|---|---|---|---|---|---|---|---|---|---|
| 31.2505 | 33.3838 | 43.529 | 40.9133 | 29.6524 | 32.5758 | 31.1883 | 28.9961 | 27.0782 | 29.8927 |
| 35.6067 | 33.7119 | 30.0046 | 43.3249 | 28.9873 | 27.8187 | 38.5344 | 35.8998 | 32.2599 | 34.3001 |
| 31.2314 | 34.2106 | 43.4818 | 40.2638 | 29.6455 | 31.8861 | 31.5193 | 28.5797 | 27.5499 | 29.595 |
| 36.353 | 33.3721 | 30.351 | 43.0632 | 28.5718 | 27.026 | 38.6899 | 35.6233 | 32.1839 | 33.74 |
| 31.2173 | 33.3497 | 44.2027 | 40.9448 | 29.9909 | 32.2393 | 30.9877 | 28.9001 | 27.3692 | 29.5612 |

FIGURE 9

Training samples:

Table 5. The real output values of biochemical oxygen demand (BOD) (mg/L)

| | | | | | | | | | |
|---|---|---|---|---|---|---|---|---|---|
| 8.0232 | 5.9753 | 8.4426 | 8.7405 | 8.2811 | 6.1161 | 7.0406 | 8.0484 | 8.1406 | 6.6089 |
| 8.7405 | 8.2811 | 6.1161 | 7.0406 | 8.0484 | 8.1406 | 6.6089 | 7.5934 | 6.9266 | 7.804 |
| 7.0406 | 8.0484 | 8.1406 | 6.6089 | 7.5934 | 6.9266 | 7.804 | 7.0098 | 8.2173 | 7.1423 |
| 6.6089 | 7.5934 | 6.9266 | 7.804 | 7.0098 | 8.2173 | 7.1423 | 7.4551 | 8.0736 | 8.9072 |
| 7.804 | 7.0098 | 8.2173 | 7.1423 | 7.4551 | 8.0736 | 8.9072 | 6.9769 | 8.0409 | 5.9846 |
| 7.1423 | 7.4551 | 8.0736 | 8.9072 | 6.9769 | 8.0409 | 5.9846 | 8.493 | 8.6906 | 8.2501 |

FIGURE 10

Training samples:

Table 6. The output of biochemical oxygen demand (BOD) in the training process

| | | | | | | | | | |
|---|---|---|---|---|---|---|---|---|---|
| 8.211758 | 6.236207 | 8.069812 | 8.634037 | 8.27548 | 6.349038 | 7.064479 | 8.147262 | 8.022211 | 6.507656 |
| 7.696169 | 6.980937 | 7.694263 | 7.056347 | 8.154825 | 7.030811 | 7.465581 | 8.065837 | 8.904803 | 7.171819 |
| 7.716786 | 5.877744 | 8.489705 | 8.76297 | 8.289459 | 5.992276 | 7.089043 | 8.221998 | 8.021786 | 6.782939 |
| 7.640604 | 6.938845 | 7.960875 | 6.979125 | 7.965993 | 7.155414 | 7.319452 | 7.615937 | 8.854171 | 7.129216 |
| 8.080036 | 6.169335 | 8.711415 | 8.536483 | 8.082924 | 6.042744 | 7.00653 | 7.794725 | 8.344556 | 6.724635 |
| 7.896813 | 6.765304 | 7.906084 | 7.122234 | 8.247757 | 7.304643 | 7.159138 | 8.214803 | 8.898856 | 7.269265 |

FIGURE 11

Testing samples:

Table 7. The input of chemical oxygen demand (COD) (mg/L)

| 31.3092 | 27.8486 | 15.1202 | 70.025 | 13.6758 | 95.5464 | 60.3989 | 47.5651 | 27.1807 | 29.0054 |
|---|---|---|---|---|---|---|---|---|---|
| 70.0205 | 31.9237 | 61.8637 | 58.9326 | 23.6635 | 66.1811 | 51.3947 | 32.0774 | 27.94 | 46.5076 |
| 31.2519 | 27.3287 | 15.0642 | 70.2673 | 14.0212 | 95.7152 | 65.6421 | 47.569 | 45.3908 | 49.2161 |
| 50.3174 | 26.0145 | 54.2891 | 46.3523 | 26.0056 | 45.8857 | 46.5509 | 60.944 | 36.56 | 51.3667 |

FIGURE 12

Testing samples:

Table 8. The input of dissolved oxygen concentration (DO) (mg/L)

| 2.4896 | 2.5153 | 2.1892 | 2.0261 | 2.0324 | 2.1938 | 1.6912 | 2.162 | 2.1031 | 2.3666 |
|---|---|---|---|---|---|---|---|---|---|
| 2.0678 | 2.324 | 2.3399 | 1.6861 | 2.2419 | 2.0213 | 2.2899 | 2.4104 | 1.5502 | 2.2016 |
| 2.4456 | 2.5251 | 2.1472 | 1.9823 | 2.0774 | 2.2853 | 1.7054 | 2.1879 | 2.1328 | 2.2863 |
| 1.987 | 2.2951 | 2.3327 | 1.7207 | 2.2527 | 1.9566 | 2.3032 | 2.4793 | 1.5446 | 2.2828 |

FIGURE 13

Testing samples:

Table 9. The input of pH

| 6.6093 | 6.4104 | 6.8877 | 6.9914 | 6.5516 | 7.1651 | 7.18 | 5.6987 | 7.467 | 7.3543 |
|---|---|---|---|---|---|---|---|---|---|
| 6.9914 | 6.5516 | 7.1651 | 7.18 | 5.6987 | 7.467 | 7.3543 | 7.2689 | 5.5129 | 7.4175 |
| 7.18 | 5.6987 | 7.467 | 7.3543 | 7.2689 | 5.5129 | 7.4175 | 7.0246 | 7.2448 | 7.0571 |
| 7.3543 | 7.2689 | 5.5129 | 7.4175 | 7.0246 | 7.2448 | 7.0571 | 7.705 | 6.0055 | 5.9073 |

FIGURE 14

Testing samples:

Table 10. The input of suspended solids concentration (SS) (mg/L)

| | | | | | | | | | |
|---|---|---|---|---|---|---|---|---|---|
| 36.2803 | 33.1397 | 30.2417 | 42.9539 | 28.2665 | 27.082 | 39.3921 | 36.4561 | 32.5752 | 33.5598 |
| 31.0348 | 33.6532 | 44.1212 | 40.0154 | 29.543 | 31.919 | 31.2991 | 28.7317 | 27.6477 | 29.9009 |
| 36.047 | 33.0463 | 30.7447 | 42.739 | 28.8568 | 27.1335 | 38.8185 | 36.1256 | 32.7802 | 33.5811 |
| 31.7294 | 34.0757 | 43.7868 | 40.4359 | 29.9468 | 32.0563 | 31.1585 | 28.5108 | 27.8176 | 30.2448 |

FIGURE 15

Testing samples:

Table 11. The real output values of biochemical oxygen demand (BOD) (mg/L)

| 8.9072 | 6.9769 | 8.0409 | 5.9846 | 8.493 | 8.6906 | 8.2501 | 6.0508 | 7.0413 | 8.0157 |
|---|---|---|---|---|---|---|---|---|---|
| 5.9846 | 8.493 | 8.6906 | 8.2501 | 6.0508 | 7.0413 | 8.0157 | 8.1693 | 6.6589 | 7.5783 |
| 8.2501 | 6.0508 | 7.0413 | 8.0157 | 8.1693 | 6.6589 | 7.5783 | 6.9819 | 7.8059 | 7.0289 |
| 8.0157 | 8.1693 | 6.6589 | 7.5783 | 6.9819 | 7.8059 | 7.0289 | 8.1834 | 7.1932 | 7.4377 |

FIGURE 16

Testing samples:

Table 12. The output of biochemical oxygen demand (BOD) in the testing process

| | | | | | | | | | |
|---|---|---|---|---|---|---|---|---|---|
| 8.389383 | 6.934934 | 8.473236 | 8.995323 | 7.987149 | 5.244652 | 7.074301 | 8.076986 | 7.902372 | 6.894986 |
| 7.898487 | 7.058665 | 7.958113 | 7.203194 | 8.36768 | 6.862683 | 7.503139 | 7.405159 | 9.114145 | 7.63787 |
| 8.328307 | 6.597964 | 8.536407 | 8.773221 | 8.107065 | 5.317567 | 6.868205 | 8.527928 | 8.063137 | 6.445257 |
| 7.31156 | 7.129209 | 7.632038 | 7.381344 | 7.977381 | 7.022829 | 7.475465 | 7.878589 | 8.593271 | 7.239718 |

FIGURE 17

INTELLIGENT DETECTION METHOD FOR BIOCHEMICAL OXYGEN DEMAND BASED ON A SELF-ORGANIZING RECURRENT RBF NEURAL NETWORK

CROSS REFERENCE TO RELATED PATENT APPLICATIONS

This application claims priority to Chinese Patent Application No. 201510999765.5, filed on Dec. 27, 2015, entitled "An Intelligent detection method for Biochemical Oxygen Demand based on a Self-organizing Recurrent RBF Neural Network."

TECHNICAL FIELD

This present disclosure relates to the field of intelligent control, and more particularly to methods and systems for intelligent detection of biochemical oxygen demand (BOD) values in an urban wastewater treatment process (WWTP).

BACKGROUND

Urban WWTP not only guarantees reliability and stability of wastewater treatment systems but also meets water quality of the national discharge standards. However, influence factors are various for BOD of WWTP and relationships between various influencing factors are complex. Therefore, it is difficult to make real-time detection for BOD. This seriously affects stable operations of urban WWTP. Intelligent detection method for BOD, based on a self-organizing recurrent RBF neural network, is helpful to improve efficiency, strengthen delicacy management, and ensure the effluent quality standards of urban WWTP. The method has great economic benefits as well as significant environmental and social benefits.

Urban WWTP makes water quality to meet national discharge standards, which are mainly related to parameters such as BOD, chemical oxygen demand (COD), effluent suspended solids (SS), ammonia nitrogen (NH3-N), total nitrogen (TN) and total phosphorus (TP) and so on. BOD refers to the needed oxygen for organic decomposition within the given time. At present, detection of BOD in wastewater is mainly performed by using dilution inoculation methods and microbial sensor determination methods. However, detection cycles are generally for 5 days, which can't reflect actual situations of WWTP in real-time. Thus it is difficult to perform closed loop controls of WWTP. Moreover, it is a big challenge for detecting the values of BOD due to a large amount of pollutants in wastewater and different contents. New hardware measuring instruments may be developed to directly determine various variables of WWTP and solve detection problems of water quality parameters due to complex organic matters in wastewater. However, research and development of new sensors will be costly and may be a time-consuming operation. Hence, new methods to solve the problem, such as real-time measurement of BOD values in WWTP, has become an important topic in both academic and practical fields.

In this disclosure, an intelligent detection method for BOD is presented by building a computing model based on a self-organizing recurrent RBF neural network. The neural network uses activity degrees and independent contribution of the hidden neuron to determine whether to add or delete hidden neurons and use a fast gradient descent algorithm to ensure the accuracy of the self-organizing recurrent RBF neural network. The intelligent detection method can achieve a real-time detection for BOD, reduce the cost of measurement for wastewater treatment plants, provide a fast and efficient approach of measurement, and improve benefits of wastewater treatment plants.

SUMMARY

Implementations of the present disclosure relate to an intelligent detection method that is designed for measuring the BOD concentration based on a self-organizing recurrent RBF neural network in this disclosure. For this intelligent detection method, the inputs are variables that are easily measured and the outputs are estimates of the BOD concentration. By constructing the self-organizing recurrent RBF neural network, the implementations obtain the mapping between the auxiliary variables and the BOD concentration. In addition, the implementations can obtain real-time measurements of BOD concentration and solve problems of a long measurement cycle for BOD concentration.

(4) BOD concentration prediction;

The testing samples are used as the input of self-organizing recurrent RBF neural network, and the output of neural network is the computed values of BOD concentration.

The novelties of this disclosure contain:

(1) In order to detect BOD concentrations online with reasonable accuracy, an intelligent detection method is developed in this disclosure. The results demonstrate that BOD trends in WWTP can be predicted with reasonable accuracy using DO, SS, pH data and COD as input variables. This intelligent detection method not only solves the problem of measured online BOD concentrations with reasonable accuracy, but also gets rid of the complicated process of developing new sensors and reduces the operation cost in WWTP.

(2) This intelligent detection method is based on the self-organizing recurrent RBF neural network by exploiting the activity degree in independent contribute of hidden neurons. The implementations of this disclosure may optimize both parameters and the network size during the learning process simultaneously. Accordingly, online measurement may be performed for detection of BOD concentrations with high measurement precision and strong adaptation for environment.

This disclosure utilizes four input variables in this intelligent detection method to predict the BOD concentration. In fact, it is in the scope of this disclosure that any of the variables: oxidation-reduction potential (ORP), DO, temperature, SS, pH, COD and total nitrogen (TN), may be used to predict effluent TP concentrations. Moreover, this intelligent detection method is also able to predict the others variables in urban WWTP.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

FIGS. 6-17 show tables in accordance with implementations of the present disclosure. Tables 1-12 show the experimental data in this disclosure.

Figure 1:
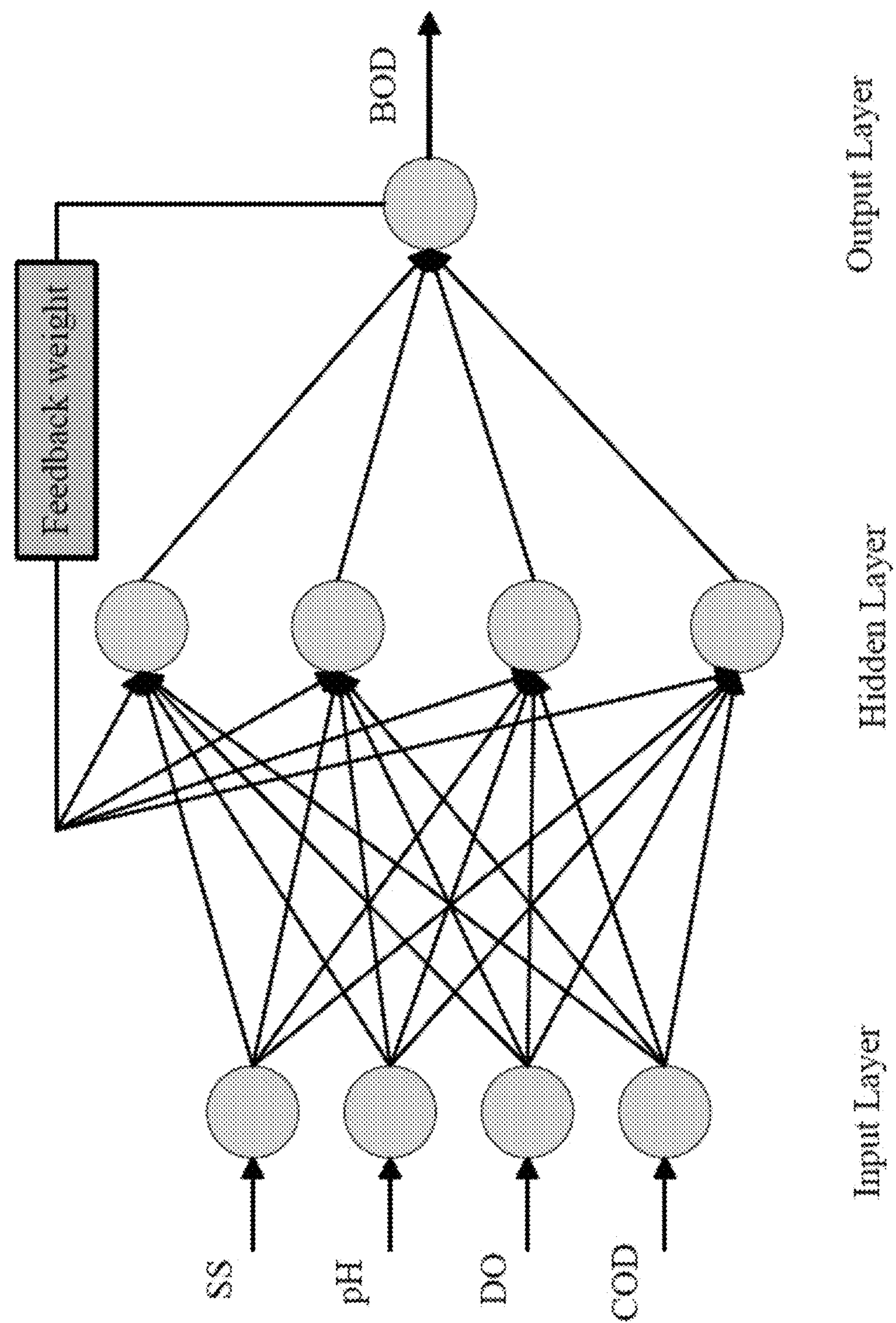
FIG. 1 shows a structure of an intelligent detection method based on a self-organizing recurrent RBF neural network in accordance with implementations of this disclosure.

Tables 1-4 show training samples of chemical oxygen demand (COD), DO, pH, SS concentration. Table 5 shows real output values of BOD concentrations. Table 6 shows outputs of the self-organizing recurrent RBF neural network in the training process. Tables 7-10 show the testing samples of chemical oxygen demand (COD), DO, pH, SS concentration. Table 11 shows real output values of BOD concentration. Table 12 shows the outputs of the self-organizing recurrent RBF neural network in the predicting process. Moreover, the samples are imported as the sequence from the tables. The first data is in the first row and the first column. Then, the second data is in the first row and the second column. Until all of data is imported from the first row, the data in the second row and following rows are inputted as the same way. To clarify, the data from Table 1 to Table 12 are re-formated and organized into training samples and testing samples in Table 13 and Table 14, respectively.

TABLE 13

The training samples of BOD

| | N | | | | | |
|---|---|---|---|---|---|---|
| Input | COD | DO | pH | SS | BOD | BOD (output) |
| 1 | 56.488 | 2.490 | 7.035 | 35.662 | 8.023 | 8.212 |
| 2 | 47.370 | 2.531 | 6.646 | 33.544 | 5.975 | 6.236 |
| 3 | 46.958 | 2.132 | 7.379 | 30.311 | 8.443 | 8.070 |
| 4 | 57.097 | 2.005 | 7.932 | 43.079 | 8.741 | 8.634 |
| 5 | 23.674 | 2.035 | 6.663 | 28.336 | 8.281 | 8.275 |
| 6 | 87.184 | 2.434 | 5.997 | 27.552 | 6.116 | 6.349 |
| 7 | 65.402 | 1.766 | 7.219 | 38.713 | 7.041 | 7.064 |
| 8 | 33.233 | 2.143 | 6.998 | 36.154 | 8.048 | 8.147 |
| 9 | 45.702 | 2.151 | 7.240 | 32.689 | 8.141 | 8.022 |
| 10 | 38.871 | 2.313 | 6.009 | 34.248 | 6.609 | 6.508 |
| 11 | 60.404 | 2.011 | 7.932 | 31.251 | 8.741 | 7.696 |
| 12 | 31.381 | 2.313 | 6.663 | 33.384 | 8.281 | 6.981 |
| 13 | 61.371 | 2.334 | 5.997 | 43.529 | 6.116 | 7.694 |
| 14 | 58.758 | 1.718 | 7.219 | 40.913 | 7.041 | 7.056 |
| 15 | 24.371 | 2.259 | 6.998 | 29.652 | 8.048 | 8.155 |
| 16 | 44.611 | 2.048 | 7.240 | 32.576 | 8.141 | 7.031 |
| 17 | 51.286 | 2.362 | 6.009 | 31.188 | 6.609 | 7.466 |
| 18 | 31.294 | 2.403 | 7.011 | 28.996 | 7.593 | 8.066 |
| 19 | 26.031 | 1.545 | 6.942 | 27.078 | 6.927 | 8.905 |
| 20 | 56.332 | 2.267 | 6.274 | 29.893 | 7.804 | 7.172 |
| 21 | 65.598 | 2.500 | 7.219 | 35.607 | 7.041 | 7.717 |
| 22 | 27.435 | 2.568 | 6.998 | 33.712 | 8.048 | 5.878 |
| 23 | 15.299 | 2.193 | 7.240 | 30.005 | 8.141 | 8.490 |
| 24 | 69.953 | 2.014 | 6.009 | 43.325 | 6.609 | 8.763 |
| 25 | 13.773 | 2.047 | 7.011 | 28.987 | 7.593 | 8.289 |
| 26 | 95.360 | 2.515 | 6.942 | 27.819 | 6.927 | 5.992 |
| 27 | 60.558 | 1.735 | 6.274 | 38.534 | 7.804 | 7.089 |
| 28 | 37.743 | 2.228 | 7.344 | 35.900 | 7.010 | 8.222 |
| 29 | 45.424 | 2.082 | 7.134 | 32.260 | 8.217 | 8.022 |
| 30 | 28.929 | 2.371 | 5.666 | 34.300 | 7.142 | 6.783 |
| 31 | 30.375 | 1.977 | 6.009 | 31.231 | 6.609 | 7.641 |
| 32 | 31.024 | 2.340 | 7.011 | 34.211 | 7.593 | 6.939 |
| 33 | 61.500 | 2.365 | 6.942 | 43.482 | 6.927 | 7.961 |
| 34 | 58.318 | 1.746 | 6.274 | 40.264 | 7.804 | 6.979 |
| 35 | 24.154 | 2.266 | 7.344 | 29.646 | 7.010 | 7.966 |
| 36 | 45.217 | 1.971 | 7.134 | 31.886 | 8.217 | 7.155 |
| 37 | 46.536 | 2.316 | 5.666 | 31.519 | 7.142 | 7.319 |
| 38 | 41.958 | 2.431 | 5.840 | 28.580 | 7.455 | 7.616 |
| 39 | 25.741 | 1.521 | 5.482 | 27.550 | 8.074 | 8.854 |
| 40 | 57.064 | 2.285 | 6.609 | 29.595 | 8.907 | 7.129 |
| 41 | 25.759 | 2.510 | 6.274 | 36.353 | 7.804 | 8.080 |
| 42 | 27.841 | 2.575 | 7.344 | 33.372 | 7.010 | 6.169 |
| 43 | 15.744 | 2.201 | 7.134 | 30.351 | 8.217 | 8.711 |
| 44 | 69.606 | 1.968 | 5.666 | 43.063 | 7.142 | 8.536 |
| 45 | 14.032 | 2.008 | 5.840 | 28.572 | 7.455 | 8.083 |
| 46 | 95.463 | 2.442 | 5.482 | 27.026 | 8.074 | 6.043 |
| 47 | 55.212 | 1.712 | 6.609 | 38.690 | 8.907 | 7.007 |
| 48 | 57.249 | 2.233 | 6.410 | 35.623 | 6.977 | 7.795 |
| 49 | 25.824 | 2.078 | 6.888 | 32.184 | 8.041 | 8.345 |
| 50 | 38.675 | 2.300 | 6.991 | 33.740 | 5.985 | 6.725 |
| 51 | 40.714 | 2.041 | 7.354 | 31.217 | 7.142 | 7.897 |
| 52 | 31.666 | 2.326 | 7.269 | 33.350 | 7.455 | 6.765 |
| 53 | 62.104 | 2.272 | 5.513 | 44.203 | 8.074 | 7.906 |
| 54 | 58.517 | 1.708 | 7.418 | 40.945 | 8.907 | 7.122 |
| 55 | 24.203 | 2.256 | 7.025 | 29.991 | 6.977 | 8.248 |
| 56 | 44.414 | 2.007 | 7.245 | 32.239 | 8.041 | 7.305 |
| 57 | 56.554 | 2.323 | 7.057 | 30.988 | 5.985 | 7.159 |
| 58 | 32.041 | 2.444 | 7.705 | 28.900 | 8.493 | 8.215 |
| 59 | 29.180 | 1.583 | 6.006 | 27.369 | 8.691 | 8.899 |
| 60 | 50.637 | 2.215 | 5.907 | 29.561 | 8.250 | 7.269 |

Testing Samples:

TABLE 14

The testing samples of BOD

| | N | | | | | |
|---|---|---|---|---|---|---|
| Input | COD | DO | pH | SS | BOD | BOD (output) |
| 1 | 31.309 | 2.490 | 6.609 | 36.280 | 8.907 | 8.389 |
| 2 | 27.849 | 2.515 | 6.410 | 33.140 | 6.977 | 6.935 |
| 3 | 15.120 | 2.189 | 6.888 | 30.242 | 8.041 | 8.473 |
| 4 | 70.025 | 2.026 | 6.991 | 42.954 | 5.985 | 8.995 |
| 5 | 13.676 | 2.032 | 6.552 | 28.267 | 8.493 | 7.987 |
| 6 | 95.546 | 2.194 | 7.165 | 27.082 | 8.691 | 5.245 |
| 7 | 60.399 | 1.691 | 7.180 | 39.392 | 8.250 | 7.074 |
| 8 | 47.565 | 2.162 | 5.699 | 36.456 | 6.051 | 8.077 |
| 9 | 27.181 | 2.103 | 7.467 | 32.575 | 7.041 | 7.902 |
| 10 | 29.005 | 2.367 | 7.354 | 33.560 | 8.016 | 6.895 |
| 11 | 70.021 | 2.068 | 6.991 | 31.035 | 5.985 | 7.898 |
| 12 | 31.924 | 2.324 | 6.552 | 33.653 | 8.493 | 7.059 |
| 13 | 61.864 | 2.340 | 7.165 | 44.121 | 8.691 | 7.958 |
| 14 | 58.933 | 1.686 | 7.180 | 40.015 | 8.250 | 7.203 |
| 15 | 23.664 | 2.242 | 5.699 | 29.543 | 6.051 | 8.368 |
| 16 | 66.181 | 2.021 | 7.467 | 31.919 | 7.041 | 6.863 |
| 17 | 51.395 | 2.290 | 7.354 | 31.299 | 8.016 | 7.503 |
| 18 | 32.077 | 2.410 | 7.269 | 28.732 | 8.169 | 7.405 |
| 19 | 27.940 | 1.550 | 5.513 | 27.648 | 6.659 | 9.114 |
| 20 | 46.508 | 2.202 | 7.418 | 29.901 | 7.578 | 7.638 |
| 21 | 31.252 | 2.446 | 7.180 | 36.047 | 8.250 | 8.328 |
| 22 | 27.329 | 2.525 | 5.699 | 33.046 | 6.051 | 6.598 |
| 23 | 15.064 | 2.147 | 7.467 | 30.745 | 7.041 | 8.536 |
| 24 | 70.267 | 1.982 | 7.354 | 42.739 | 8.016 | 8.773 |
| 25 | 14.021 | 2.077 | 7.269 | 28.857 | 8.169 | 8.107 |
| 26 | 95.715 | 2.285 | 5.513 | 27.134 | 6.659 | 5.318 |
| 27 | 65.642 | 1.705 | 7.418 | 38.819 | 7.578 | 6.868 |
| 28 | 47.569 | 2.188 | 7.025 | 36.126 | 6.982 | 8.528 |
| 29 | 45.391 | 2.133 | 7.245 | 32.780 | 7.806 | 8.063 |
| 30 | 49.216 | 2.286 | 7.057 | 33.581 | 7.029 | 6.445 |
| 31 | 50.317 | 1.987 | 7.354 | 31.729 | 8.016 | 7.312 |
| 32 | 26.015 | 2.295 | 7.269 | 34.076 | 8.169 | 7.129 |

TABLE 14-continued

| The testing samples of BOD | | | | | | |
|---|---|---|---|---|---|---|
| | N | | | | | |
| Input | COD | DO | pH | SS | BOD | BOD (output) |
| 33 | 54.289 | 2.333 | 5.513 | 43.787 | 6.659 | 7.632 |
| 34 | 46.352 | 1.721 | 7.418 | 40.436 | 7.578 | 7.381 |
| 35 | 26.006 | 2.253 | 7.025 | 29.947 | 6.982 | 7.977 |
| 36 | 45.886 | 1.957 | 7.245 | 32.056 | 7.806 | 7.023 |
| 37 | 46.551 | 2.303 | 7.057 | 31.159 | 7.029 | 7.475 |
| 38 | 60.944 | 2.479 | 7.705 | 28.511 | 8.183 | 7.879 |
| 39 | 36.560 | 1.545 | 6.006 | 27.818 | 7.193 | 8.593 |
| 40 | 51.367 | 2.283 | 5.907 | 30.245 | 7.438 | 7.240 |

DETAILED DESCRIPTION

This disclosure takes suspended solids concentrations (SS), dissolved oxygen (DO), pH, chemical oxygen demand (COD) as characteristic variables for BOD, except for the pH (no unit), the unit of the above parameters is mg/L;

The experimental data comes from water quality analysis statement of a wastewater treatment plant in 2012; choosing data of SS concentrations, DO, pH and COD as experimental samples, after eliminating abnormal sample, 100 groups of data are available, and the group of 60 are used as training samples, and the remaining 40 groups are used as test samples.

This disclosure adopts the following technical scheme and implementation steps:

An intelligent detection method for the BOD concentration based on a self-organizing recurrent RBF neural network is described using the following operations.

(1) Determining the input and output variables of BOD: For sewage treatment process of activated sludge system, sewage treatment process variables are analyzed and select the input variables of BOD computing model: DO concentration, effluent SS concentration, pH, COD. The output value of computing model is the detected BOD concentration.

(2) Computing model of intelligent detection of BOD: establishing a computing model of BOD based on a self-organizing recurrent RBF neural network. The structure of recurrent RBF neural network may include three layers: input layer, hidden layer and output layer. The network is 4-m−1, named the number of input layer is 4 and hidden neurons is m. Connection weights between input layer and hidden layer are assigned one, the connection weights between hidden layer and output layer randomly assign values, the assignment interval is [1, 1]. The number of the training sample is N and the input of self-organizing recurrent RBF neural network is $x(t)=[x_1(t), x_2(t), x_3(t), x_4(t)]$ at time t. The expectation output of neural network output is expressed as $y_d(t)$ and the actual output is expressed as y(t). Computing method of BOD can be described:

① The input Layer: There are 4 neurons which represent the input variables in this layer. The output values of each neuron are as follows:

$$u_i(t)=x_i(t) \quad \text{(Equation 1)}$$

wherein $u_i(t)$ is the ith output value at time t, i=1, 2, . . . , 4, and the input vector is $x(t)=[x_1(t), x_2(t), \ldots, x_4(t)]$.

② The Hidden Layer: There are m neurons of hidden layer. The outputs of hidden neurons are:

$$\theta_j(t) = e^{-\frac{\|h_j(t)-c_j(t)\|^2}{2\sigma_j^2(t)}}, \quad j = 1, 2, \ldots, m \quad \text{(Equation 2)}$$

$c_j(t)$ denotes the center vector of the jth hidden neuron and $c_j(t)=[c_{1j}(t), c_{2j}(t), \ldots, c_{4j}(t)]^T$ at time t, $\|h_j(t)-c_j(t)\|$ is the Euclidean distance between $h_j(t)$ and $c_j(t)$, and $\sigma_j(t)$ is the radius or width of the jth hidden neuron at time t, $h_j(t)$ is input vector of the jth hidden neuron at time t described as $$h_j(t)=[u_1(t),u_2(t), \ldots u_4(t),v_j(t)\times y(t-1)]^T, \quad \text{(Equation 3)}$$

y(t−1) is the output value of the output layer at time t−1, $v_j(t)$ denotes the connection weight from output layer to the jth hidden neuron at time t, and $v(t)=[v_1(t), v_2(t), \ldots, v_m(t)]^T$, T represents transpose;

③ The Output Layer: There is only one node in this layer, the output is:

$$y(t) = f(w(t), \theta(t)) = \sum_{j=1}^{m} w_j(t)\times\theta_j(t), \quad j = 1, \ldots, m, \quad \text{(Equation 4)}$$

wherein $w(t)=[w_1(t), w_2(t), \ldots, w_m(t)]^T$ is the connection weights between the hidden neurons and output neuron at time t, $\theta(t)=[\theta_1(t), \theta_2(t), \ldots, \theta_m(t)]^T$ is the output vector of the hidden layer, y(t) represents the output of recurrent RBF neural network at time t.

The error of self-organizing recurrent RBF neural network is:

$$E(t) = \frac{1}{N}\sum_{t=1}^{N}(y_d(t) - y(t))^2, \quad \text{(Equation 5)}$$

$y_d(t)$ is the expectation output of neural network and the actual output is expressed as y(t);

(3) Training the self-organizing recurrent RBF neural network;

① Providing the self-organizing recurrent RBF neural network, the initial number of hidden layer neurons is m, and m>2 is a positive integer. The input of self-organizing recurrent RBF neural network is x(1), x(2), . . . , x(t), . . . , x(N), correspondingly, the expectation output is $y_d(1)$, $y_d(2)$, . . . , $y_d(t)$, . . . , $y_d(N)$, expected error value is set to $E_d$, $E_d \in (0, 0.01)$. The every variable of initial centre value $c_j(1) \in (-2, 2)$, width value $\sigma_j(1) \in (0, 1)$, initial feedback weight $v_j(1) \in (0, 1)$, j=1, 2, . . . , m; initial weight $w(1) \in (0, 1)$;

② Setting the learning step s=1;

③ t=s; According to Equations (1)-(4), calculating the output of self-organizing recurrent RBF neural network by exploiting a fast gradient descent algorithm:

$$c_j(t+1) = c_j(t) - \eta_c\frac{1}{\sigma_j^2}(y_d(t) - y(t))w_j(t)\times\theta(t)[h_j(t) - c_j(t)], \quad \text{(Equation 6)}$$

$$\sigma_j(t+1) = \sigma_j(t) - \eta_\sigma\frac{1}{\sigma_j^3}(y_d(t) - y(t))w_j(t)\times w_j(t)\times\theta(t)\|h_j(t) - c_j(t)\|^2, \quad \text{(Equation 7)}$$

$$v_j(t+1) = v_j(t) - \eta_v(y_d(t) - y(t))w_j(t)\theta(t)y(t-1), \quad \text{(Equation 8)}$$

$$w_j(t+1) = w_j(t) - \eta_w(y_d(t) - y(t))\theta_j(t), \quad \text{(Equation 9)}$$

$\eta_c$, $\eta_\sigma$, $\eta_v$, $\eta_w$ are the learning rate of center, width, feedback connection weight from output layer to hidden layer and the connection weight between hidden layer and output layer, respectively. In addition, $\eta_c \in (0, 0.01]$, $\eta_\sigma \in (0, 0.01]$, $\eta_v \in (0, 0.02]$, $\eta_w \in (0, 0.01]$; $c_j(t+1)=[c_{1j}(t+1), c_{2j}(t+1), \ldots, c_{4j}(t+1)]$ denotes the center vector of the jth hidden neuron at time t+1; $\sigma_j(t+1)$ is the radius or width of the jth hidden neuron at time t+1; $v_j(t+1)$ denotes the connection weight from output layer to the jth hidden neuron at time t+1; $w_j(t+1)$ is the connection weights between the hidden neurons and output neuron at time t+1;

④ t>3, calculating independent contribution:

$$\psi_j(t) = \frac{q_j(t-1)+q_j(t)}{\sum_{j=1}^{m}(q_j(t-1)+q_j(t))}, \quad j=1, \ldots, m, \tag{Equation 10}$$

wherein $\psi_j(t)$ is the independent contribution of the jth hidden neuron at time t; $q_j(t-1)$ is independent contribution output of the jth hidden neuron at time t−1. $q_j(t)$ is independent contribution output of the jth hidden neuron at time t; Moreover, $g_j=[q_j(t-1), q_j(t)]$ is independent contribution output vector of the jth hidden neuron; $Q(t)=[q_1(t), \ldots q_{m-1}(t), q_m(t)]^T$ is the independent contribution matrix at time t, $$Q(t)=\Phi(t)\Omega(t), \tag{Equation 11}$$

wherein $\Omega(t)$ is a coefficients matrix which is provided as:

$$\Omega(t)=D^{-1}(t)\Phi((t)B(t)z(t), \tag{Equation 12}$$

wherein $\phi(t)=[\theta(t-1), \theta(t)]$ is output matrix of hidden layer at time t, $\theta(t-1)=[\theta_1(t-1), \theta_2(t-1), \ldots, \theta_m(t-1)]^T$ is output vector of hidden layer at time t−1, $\theta(t)=[\theta_1(t), \theta_2(t), \ldots, \theta_m(t)]^T$ is output vector of hidden layer at time t; D(t), B(t) and z(t) are the covariance matrix of ((t), the whitening matrix of y(t) and the whitening transformation matrix of y(t), respectively. D(t), B(t) and z(t) are provided as:

$$D(t) = \begin{bmatrix} \frac{\sum_{j=1}^{m}(\theta_j(t-1)-\overline{\theta}(t-1))^2}{m-1} & \frac{\sum_{j=1}^{m}(\theta_j(t-1)-\overline{\theta}(t-1))(\theta_j(t)-\overline{\theta}(t))}{m-1} \\ \frac{\sum_{j=1}^{m}(\theta_j(t-1)-\overline{\theta}(t-1))(\theta_j(t)-\overline{\theta}(t))}{m-1} & \frac{\sum_{j=1}^{m}(\theta_j(t)-\overline{\theta}(t))^2}{m-1} \end{bmatrix}, \tag{Equation 13}$$

$$B(t) = \Lambda^{-1/2}(t)U^T(t), \tag{Equation 14}$$

$$z(t) = \Lambda^{-1/2}(t)U^T(t)y(t), \tag{Equation 15}$$

wherein $\overline{\theta}(t-1)=(\theta_1(t-1)+\theta_2(t-1)+ \ldots +\theta_m(t-1))/m$ is the average value of elements of output vector in hidden layer at time t−1, $\overline{\theta}(t)=(\theta_1(t)+\theta_2(t)+ \ldots +\theta_m(t))/m$ is the average value of elements of output vector in hidden layer at time t; U(t) and $\Lambda(t)$ are the eigenvector and eigenvalue matrices of y(t); y(t) is the output matrix of self-organizing recurrent RBF neural network at time t, $$y(t)=\Phi(t)\delta(t), \tag{Equation 16}$$

wherein $\delta(t)$ is the weight matrix of hidden layer to output layer, $$\delta(t)=[w(t-1),w(t)], \tag{Equation 17}$$

wherein $w(t-1)=[w_1(t-1), w_2(t-1), \ldots, w_m(t-1)]^T$ and $w(t)=[w_1(t), w_2(t), \ldots, w_m(t)]^T$ are the output of self-organizing recurrent RBF neural network, the output vector of the hidden layer and the weight vector at time t−1 and time t, respectively.

⑤ t>3, calculating activity degree of hidden neuron:

$$S_j(t)=e^{-\|h_j(t)-c_j(t)\|}, \tag{Equation 18}$$

wherein $S_j(t)$ is the activity degree of the jth hidden neuron at time t, j=1, 2, . . . , m.

⑥ t>3, adjusting the structure of the self-organizing recurrent RBF neural network:

In the process of adjusting structure of neural network, calculating the activity degree of the lth hidden neuron $S_l(t)$ and the independent contribution of the lth hidden neuron $\psi_l(t)$.

When the activity degree and independent contribution of the lth hidden neuron satisfy:

$$S_l(t)=\max S(t), \tag{Equation 19}$$

$$\psi_l(t)=\max \psi(t), \tag{Equation 20}$$

wherein $S(t)=[S_1(t), \ldots, S_{m-1}(t), S_m(t)]$ is the vector of activity degree of hidden neurons at time t, $\psi(t)=[\psi_l(t), \ldots, \psi_{m-1}(t), \psi_m(t)]$ is the vector of independent contribution of hidden neurons at time t; adding one hidden neuron and the number of hidden neurons is $M_1=m+1$; Otherwise, the structure of self-organizing recurrent RBF neural network is not adjusted, $M_1=m$;

When the activity degree and independent contribution of the ith hidden neuron satisfy:

$$S_i(t)=\min S(t), \tag{Equation 21}$$

$$\psi_i(t)=\min \psi(t), \tag{Equation 22}$$

deleting the ith hidden neuron and updating the number of hidden neurons $M_2=M_1-1$; otherwise the structure of self-organizing recurrent RBF neural network is not adjusted, $M_2=M_1$;

⑦ increasing one learning step s, if s<N, then turning to step ③; if s=N, turning to step ⑧.

⑧ according to Eq. (5), calculating the performance of self-organizing recurrent RBF neural network. If $E(t) \geq E_d$, then turning to step ③; if $E(t) < E_d$, stopping the training process.

Figure 2:
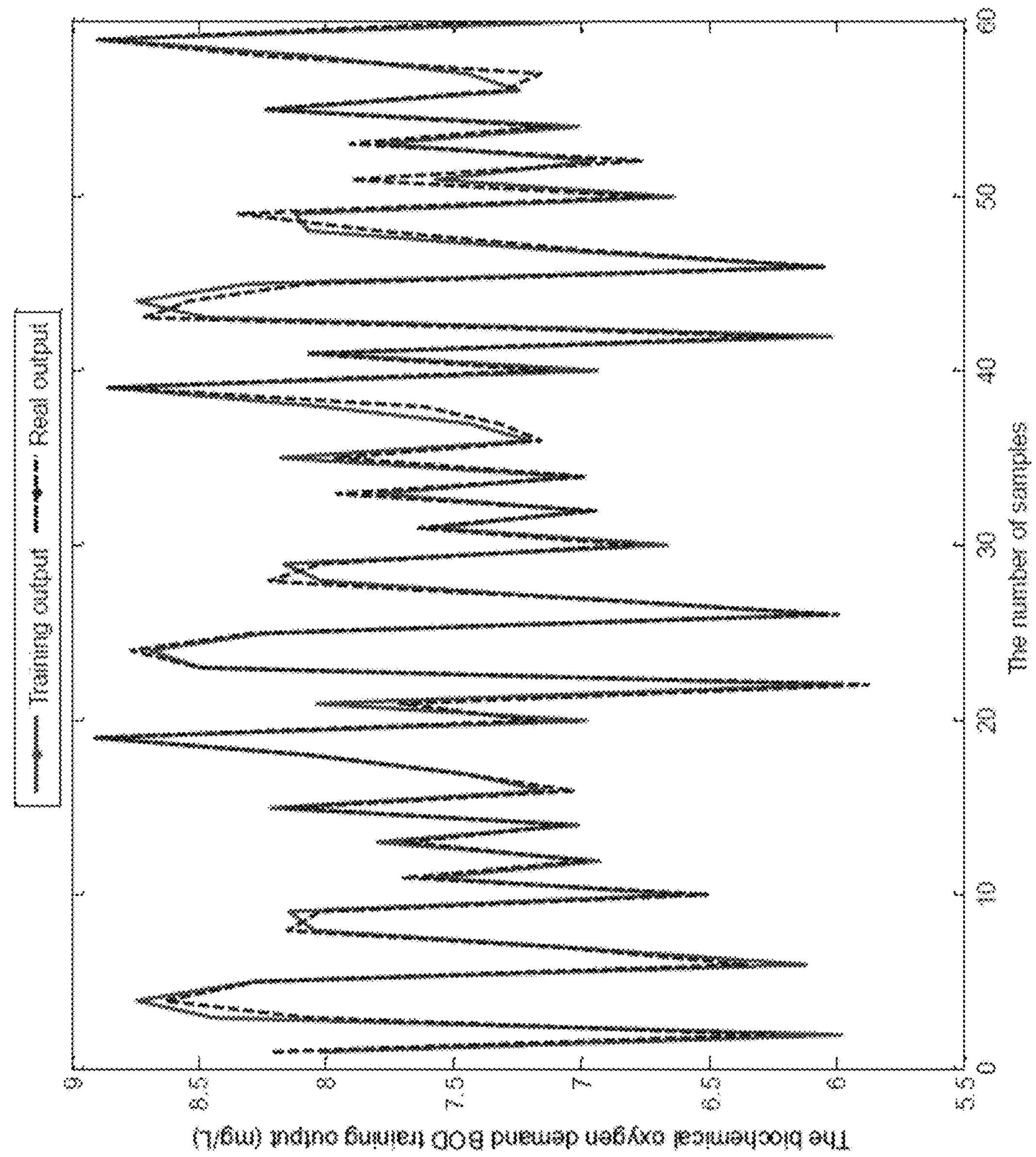
FIG. 2 shows training results of an intelligent detection method.
Figure 3:
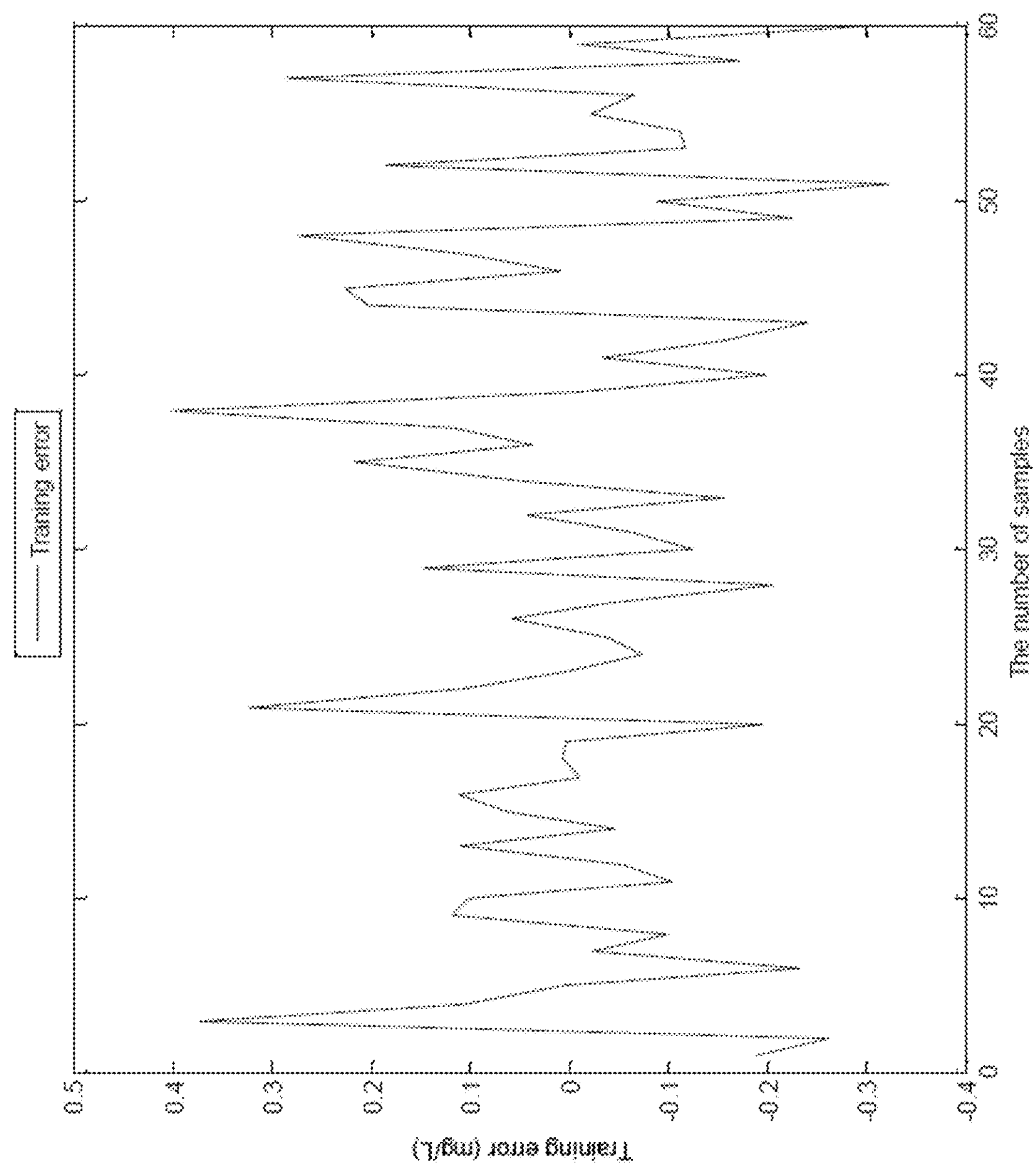
FIG. 3 shows a training error of an intelligent detection method.

The training result of the intelligent detection method for BOD concentration is shown in FIG. 2. X axis shows the number of samples. Y axis shows the BOD concentration. The unit of Y axis is mg/L. The solid line presents the real values of BOD concentrations. The dotted line shows the outputs of intelligent detection method in the training process. The errors between the real values and the outputs of intelligent detection method in the training process are shown in FIG. 3. X axis shows the number of samples. Y axis shows the training error. The unit of Y axis is mg/L.

Figure 4:
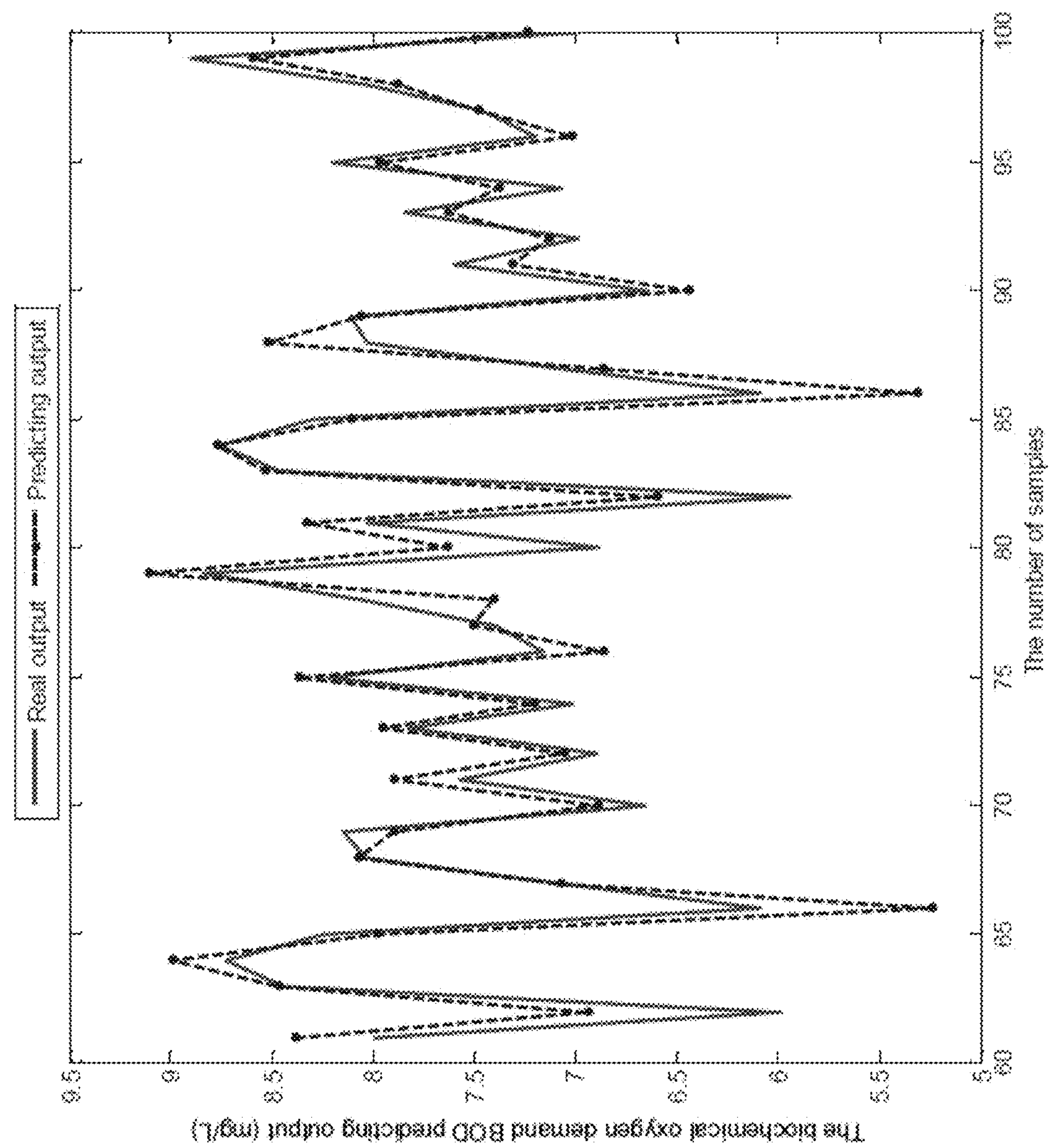
FIG. 4 shows a predicting result of an intelligent detection method.
Figure 5:
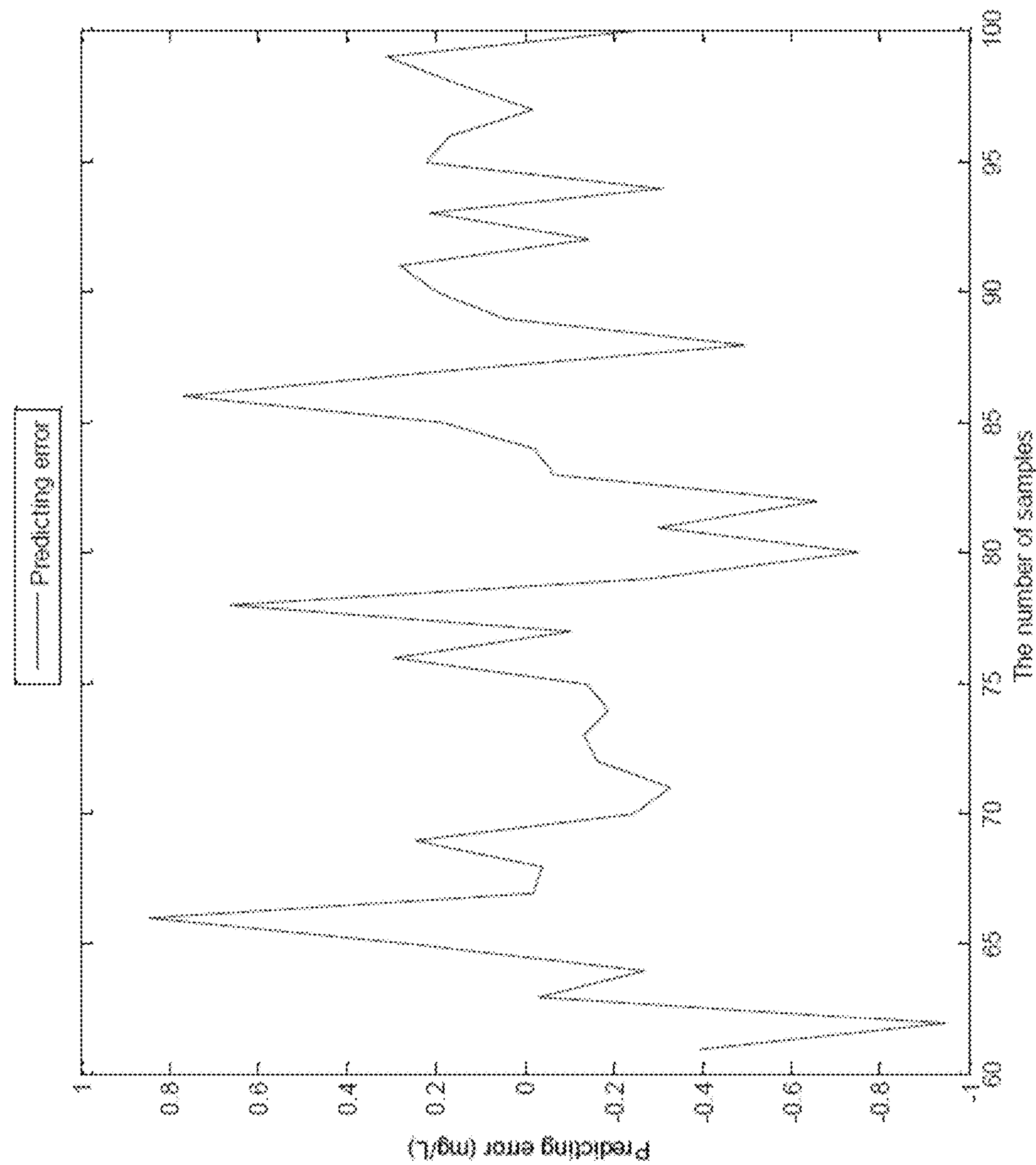
FIG. 5 shows a predicting error of an intelligent detection method.

(4) BOD Concentration Prediction;

The testing samples used as the input of self-organizing recurrent RBF neural network, the output of neural network is the computing values of BOD concentration. The predicting result is shown in FIG. 4. X axis shows the number of testing samples. Y axis shows the BOD concentration. The unit of Y axis is mg/L. The solid line presents the real values of BOD concentration. The dotted line shows the outputs of intelligent detection method in the testing process. The errors between the real values and the outputs of intelligent detection method in the testing process are shown in FIG. 5. X axis shows the number of samples. Y axis shows the testing error. The unit of Y axis is mg/L.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

What is claimed is:

1. A method for intelligent detection of a biochemical oxygen demand (BOD) concentration, the method comprising:

(1) determining input and output variables of BOD by analyzing sewage treatment process variables and selecting the input variables of a BOD computing model that include a dissolved oxygen concentration (DO), an effluent suspended solids concentration (SS), a pH value, a chemical oxygen demand (COD) for a sewage treatment process of an activated sludge system, an output value of the BOD computing model being a detected BOD concentration associated with the sewage treatment process of the activated sludge system within the ranges of DO=[0.2., 8], SS=[0.5, 100], pH=[6, 8], COD=[0, 200], BOD=[0, 100];

(2) designing the BOD computing model of the intelligent detection of the BOD concentration using a self-organizing recurrent Radial basis function (RBF) neural network, a structure of the recurrent RBF neural network comprising an input layer comprising input layer neurons, a hidden layer comprising hidden neurons, and an output layer comprising an output neuron;

(3) training the self-organizing recurrent RBF neural network using training samples, a number of the training samples denoted by N, comprising:

(1) providing the self-organizing recurrent RBF neural network, an initial number of the hidden layer neurons is m, m>2 is a positive integer, input of the self-organizing recurrent RBF neural network is x(1), x(2), . . . , x(t), . . . , x(N), correspondingly, the expectation output is $y_d(1)$, $y_d(2)$, . . . $y_d(t)$, . . . $y_d(N)$, an expected error value is set to $E_d$, $E_d \in (0, 0.01)$, each variable of initial center values $c_j(1) \in (-2, 2)$, a width value $o'_j(1) \in (0, 1)$, an initial feedback weight $v_j(1) \in (0, 1)$, j=1, 2, . . . , m, and an initial weight $w(1) \in (0, 1)$;

(2) setting a learning step S=1;

(3) t=s, calculating the output of the self-organizing recurrent RBF neural network by exploiting a fast gradient descent algorithm using parameters:

$$c_j(t+1) = c_j(t) - \eta_c \frac{1}{\sigma_j^2}(y_d(t) - y(t))w_j(t) \times \theta(t)[h_j(t) - c_j(t)], \quad \text{(Equation 6)}$$

$$\sigma_j(t+1) = \sigma_j(t) - \eta_\sigma \frac{1}{\sigma_j^3}(y_d(t) - y(t))w_j(t) \times w_j(t) \times \theta(t)\|h_j(t) - c_j(t)\|^2, \quad \text{(Equation 7)}$$

$$v_j(t+1) = v_j(t) - \eta_v(y_d(t) - y(t))w_j(t)\theta(t)y(t-1), \quad \text{(Equation 8)}$$

$$w_j(t+1) = w_j(t) - \eta_w(y_d(t) - y(t))\theta_j(t), \quad \text{(Equation 9)}$$

wherein, $\eta_c$, $\eta_{o'}$, $\eta_v$, $\eta_w$ are the learning rate of center, width, feedback connection weight from the output layer to the hidden layer and connection weight between the hidden layer and the output layer, respectively, $\eta_c \in (0, 0.01]$, $\eta_o \in (0, 0.01]$, $\eta_v \in (0, 0.02]$, $\eta_w \in (0, 0.01]$, $c_j(t+1)=[c_{1j}(t+1), c_{2j}(t+1), \ldots c_{4j}(t+1)]$ denotes a center vector of the jth hidden neuron at time t+1, $o'_j(t+1)$ is a radius or width of the jth hidden neuron at time t+1, $v_j(t+1)$ denotes a connection weight from output layer to the jth hidden neuron at time t+1, and $w_j(t+1)$ is the connection weights between the hidden neurons and the output neuron at time t+1;

(4) t>3, calculating independent contribution of the jth hidden neuron at time t, j=1, . . . m;

(5) t>3, calculating activity degree of the hidden neuron:

$$S_j(t) = e - \|h_j(t) - c_j(t)\|, \quad \text{(Equation 18)}$$

wherein $S_j(t)$ is the activity degree of the jth hidden neuron at time t, j=1, 2, . . . , m;

(6) t>3, adjusting the structure of the self-organizing recurrent RBF neural network by calculating the activity degree of the lth hidden neuron S(t) and the independent contribution of the lth hidden neuron $\psi_l(t)$, wherein the activity degree and independent contribution of the lth hidden neuron satisfy:

$$S_l(t) = \max S(t), \quad \text{(Equation 19)}$$

$$\psi_l(t) = \max \psi(t), \quad \text{(Equation 20)},$$

wherein $S(t)=[S_1(t), \ldots, S_m-1(t), S_m(t)]$ is a vector of activity degree of hidden neurons at time t, $\psi(t)=[\psi(t), \ldots, \psi_m-1(t), \psi_m(t)]$ is a vector of independent contribution of the hidden neurons at time t, one of the hidden neurons is added and the number of hidden neurons is updated using $M_1$=m+1 or the structure of self-organizing recurrent RBF neural network is not adjusted, $M_1$=m, when the activity degree and independent contribution of the ith hidden neuron satisfy:

$$S_i(t) = \min S(t), \quad \text{(Equation 21)}$$

$$\psi_i(t) = \min \psi(t), \quad \text{(Equation 22)}$$

wherein the ith hidden neuron is deleted and the number of the hidden neurons is updated using $M_2=M_1-1$ or the structure of self-organizing recurrent RBF neural network is not adjusted, $M_2=M_1$;

(6) increasing a learning steps:

if s<N, turning to step (3)

if s=N, turning to step (8); and (8) calculating error E(t) of the self-organizing recurrent RBF neural network:

if E(t)≥Ed, then returning to step (3); and if E(t)<Ed, stopping the training; and (4) inputting into the trained self-organizing RBF neural network values of the input variables associated with at least one testing sample associated with the sewage treatment process of the activated sludge system and computing the output value of the trained self-organizing RBF neural network into which the values of the input variables were entered as the BOD concentration associated with the at least one testing sample, wherein the sewage treatment process is controlled based on the BOD concentration associated with the at least one testing sample.

2. The method of claim 1, wherein a connection manner of the self-organizing recurrent RBF neural network is 4-m−1 in which a number of the input neurons in the input layer is 4 and a number of hidden neurons in the hidden layer is m, connection weights between the input layer and the hidden layer are assigned 1, the connection weights between the hidden layer and the output layer are randomly assigned values, and the assignment interval is [1, 1].

3. The method of claim 1, wherein the expectation output of the self-organizing recurrent RBF neural network is expressed as $y_d(t)$ and an actual output of the self-organizing recurrent RBF neural network is expressed as y(t), and the BOD concentration is calculated based on the self-organizing recurrent RBF neural network comprising:

(1) the input layer comprising the 4 neurons representing the input variables in the input layer, and the output values of each neuron of the input layer are as follows:

$$u_i(t)=x_i(t); \quad \text{(Equation 1)}$$

wherein u(t) is a ith output value at time t, i=1, 2, . . . 4, and an input vector is $x(t)=[x_1(t), x_2(t), \ldots, x_4(t)]$, (2) the hidden layer comprising the m hidden neurons of the hidden layer, the outputs of hidden neurons are:

$$\theta_j(t) = e^{-\frac{\|h_j(t)-c_j(t)\|^2}{2\sigma_j^2(t)}}, \quad j = 1, 2, \ldots, m, \quad \text{(Equation 2)}$$

Θ denotes the outputs of hidden neurons, $c_j(t)$ denotes the center vector of the jth hidden neuron and $c_j(t)=[c_j(t), c_{2j}(t), \ldots c_{4j}(t)]^T$ at time t, $\|h_j(t)-c_j(t)\|$ is the Euclidean distance between $h_j(t)$ and $c_j(t)$, $o'_j(t)$ is the radius or width of the jth hidden neuron at time t, and $h_j(t)$ is input vector of the jth hidden neuron at time t described as $$h_j(t)=[u_1(t),u_2(t), \ldots ,u_4(t),v_j(t)\times y(t-1)]^T, \quad \text{(Equation 3)}$$

wherein y(t−1) is the output value of the output layer at time t−1, $v_j(t)$ denotes the connection weight from output layer to the jth hidden neuron at time t, and $v(t)=(v_1(t), v_2(t), \ldots, v_m(t)]^T$, T represents transpose;

(3) the output layer comprising one node, the output is:

$$y(t) = f(w(t), \theta(t)) = \sum_{j=1}^{m} w_j(t)\times\theta_j(t), \quad j = 1, \ldots, m, , \quad \text{(Equation 4)}$$

wherein $w(t)=[w_1(t), w_2(t), \ldots, w_m(t)]^T$ is the connection weights between the hidden neurons and output neuron at time t, $\theta(t)=[0_1(t), 0_2(t), \ldots, 0_m(t)]^T$ is the output vector of the hidden layer, and y(t) represents the output of recurrent RBF neural network at time t, and j is the number of the hidden neurons.

4. The method of claim 1, wherein an error of the self-organizing recurrent RBF neural network is calculated using:

$$E(t) = \frac{1}{N}\sum_{t=1}^{N}(y_d(t) - y(t))^2, \quad \text{(Equation 5)}$$

wherein $y_d(t)$ is the expectation output of neural network and the actual output is expressed as y(t), and E is the sum of squared errors between the predicted outputs and the real outputs.

5. A method for intelligent detection of a biochemical oxygen demand (BOD) concentration, comprising:

(1) Determining input and output variables of BOD by analyzing sewage treatment process variables and selecting the input variables of a BOD computing model that include a dissolved oxygen concentration (DO), and effluent suspended solids concentration (SS), a pH value, a chemical oxygen demand (COD) for a sewage treatment process of an activated sludge system, an output value of the BOD computing model being a detected BOD concentration associated with the sewage treatment process of the activated sludge system, within the ranges of DO=[0.2, 8], SS=[0.5, 100], pH=[6, 8], COD=[0, 200], BOD=[0, 100];

(2) designing the BOD computing model of the intelligent detection of the BOD concentration using a self-organizing recurrent Radial basis function (RBF) neural network, a structure of the recurrent RBF neural network comprising an input layer comprising input layer neurons, a hidden layer comprising hidden neurons, and an output layer comprising an output neuron;

(3) training the self-organizing recurrent RBF neural network using training samples, a number of the training samples denoted by N, further comprising the steps of:

(1) providing the self-organizing recurrent RBF neural network, an initial number of the hidden layer neurons is m, m>2 is a positive integer, the input of the self-organizing recurrent RBF neural network is x(1), x(2), . . . , x(t), . . . , x(N), correspondingly, the expectation output is $y_d(1), y_d(2), \ldots y_d(t), \ldots y_d(N)$, an expected error value is set to $E_d$, $E_d \in (0, 0.01)$, each variable of initial center values $c_j(1) \in (-2, 2)$, a width value $o'_j(1) \in (0, 1)$, an initial feedback weight $v_j(1) \in (0, 1)$, j=1, 2, . . . , m; and an initial weight $w(1) \in (0, 1)$;

(2) setting a learning step S=1;

(3) t=s, calculating the output of the self-organizing recurrent RBF neural network according to equations (1)-(4) and exploiting a fast gradient descent algorithm using parameters:

$$c_j(t+1) = c_j(t) - \eta_c\frac{1}{\sigma_j^2}(y_d(t) - y(t))w_j(t)\times\theta(t)[h_j(t) - c_j(t)], \quad \text{(Equation 6)}$$

$$\sigma_j(t+1) = \sigma_j(t) - \eta_\sigma\frac{1}{\sigma_j^3}(y_d(t) - y(t))w_j(t)\times w_j(t)\times\theta(t)\|h_j(t) - c_j(t)\|^2, \quad \text{(Equation 7)}$$

$$v_j(t+1) = v_j(t) - \eta_v(y_d(t) - y(t))w_j(t)\theta(t)y(t-1), \quad \text{(Equation 8)}$$

$$w_j(t+1) = w_j(t) - \eta_w(y_d(t) - y(t))\theta_j(t), \quad \text{(Equation 9)}$$

wherein, $\eta_c$, $\eta_{o'}$, $\eta_v$, $\eta_w$ are the learning rate of center, width, feedback connection weight from the output layer to the hidden layer and the connection weight between the hidden layer and the output layer, respectively, $\eta_c \in (0, 0.01]$, $\eta_o \in (0, 0.01]$, $\eta_v \in (0, 0.02]$, $\eta_w \in (0, 0.01]$, $c_j(t+1)=[c_{1j}(t+1), c_{2j}(t+1), \ldots c_{4j}(t+1)]$ denotes the center vector of the jth hidden neuron at time t+1, $o'_j(t+1)$ is a radius or width of the jth hidden neuron at time t+1, $v_j(t+1)$ denotes the connection weight from output layer to the jth hidden neuron at time t+1, and $w_j(t+1)$ is the connection weights between the hidden neurons and output neuron at time t+1;

(4) t>3, calculating independent contribution:

$$\psi_j(t) = \frac{q_j(t-1)+q_j(t)}{\sum_{j=1}^{m}(q_j(t-1)+q_j(t))}, \quad j = 1, \ldots, m, \qquad \text{(Equation 10)}$$

wherein $\psi_j(t)$ is the independent contribution of the jth hidden neuron at time t, $q_i(t-1)$ is independent contribution output of the jth hidden neuron at time t−1, $q_i(t)$ is independent contribution output of the jth hidden neuron at time t, $q_j=[q_j(t-1), q_j(t)]$ is independent contribution output vector of the jth hidden neuron, $Q(t)=[q_1(t), \ldots q_{m-1}(t), q_m(t)]^T$ is the independent contribution matrix at time t, $$Q(t)=\Phi(t)\Omega(t), \qquad \text{(Equation 11)}$$

wherein $\Omega(t)$ is a coefficients matrix which is provided as:

$$\Omega(t)=D^{-1}(t)\Phi(t)B(t)z(t), \qquad \text{(Equation 12)}$$

wherein $\Phi(t)=[\theta(t-1), \theta(t)$ is output matrix of hidden layer at time t, $0(t-1)=[\theta_1(t-1), \theta_2(t-1), \ldots, \theta_m(t-1)]^T$ is output vector of hidden layer at time t−1, $\theta(t)=[\theta_1(t), \theta_2(t), \ldots, \theta_m(t)$ is output vector of hidden layer at time t, D(t), B(t) and z(t) are the covariance matrix of $\Phi(t)$, the whitening matrix of y(t) and the whitening transformation matrix of y(t), respectively, and D(t), B(t) and z(t) are provided as:

$$D(t) = \begin{bmatrix} \frac{\sum_{j=1}^{m}(\theta_j(t-1)-\overline{\theta}(t-1))^2}{m-1} & \frac{\sum_{j=1}^{m}(\theta_j(t-1)-\overline{\theta}(t-1))(\theta_j(t)-\overline{\theta}(t))}{m-1} \\ \frac{\sum_{j=1}^{m}(\theta_j(t-1)-\overline{\theta}(t-1))(\theta_j(t)-\overline{\theta}(t))}{m-1} & \frac{\sum_{j=1}^{m}(\theta_j(t)-\overline{\theta}(t))^2}{m-1} \end{bmatrix}, \qquad \text{(Equation 13)}$$

$$B(t) = \Lambda^{-1/2}(t)U^T(t), \qquad \text{(Equation 14)}$$

$$z(t) = \Lambda^{-1/2}(t)U^T(t)y(t), \qquad \text{(Equation 15)}$$

wherein $\theta(t-1)=\theta_1(t-1)+\theta_2(t-1)+\ldots+\theta_m(t-1))/m$ i is the average value of elements of output vector in the hidden layer at time t−1, $6(t)=(0(0+0(0+\ldots+0, (t))/m$ is the average value of elements of the output vector in the hidden layer at time t, U(t) and A(t) are the eigenvector and eigenvalue matrices of y(t), y(t) is the output matrix of the self-organizing recurrent RBF neural network at time t, $$y(t)=\Phi(t)\delta(t), \qquad \text{(Equation 16)}$$

wherein $\delta(t)$ is the weight matrix of hidden layer to the output layer, $$\delta(t)=[w(t-1),w(t)], \qquad \text{(Equation 17)}$$

wherein $w(t-1)=[w_1(t-1), w_2(t-1), \ldots, w_m(t-1)]^T$ and $w(t)=[w_1(t), w_2(t), \ldots, w_m(t)]^T$ are the output of self-organizing recurrent RBF neural network, the output vector of the hidden layer and the weight vector at time t−1 and time t, respectively, (5) t>3, calculating activity degree of the hidden neuron:

$$S_j(t)=e-\|h_j(t)-c_j(t)\|, \qquad \text{(Equation 18)}$$

wherein $S_j(t)$ is the activity degree of the jth hidden neuron at time t, j=1, 2, . . . , m, (6) t>3, adjusting the structure of the self-organizing recurrent RBF neural network by calculating the activity degree of the lth hidden neuron S(t) and the independent contribution of the lth hidden neuron $\psi_l(t)$, wherein the activity degree and independent contribution of the lth hidden neuron satisfy:

$$S_l(t)=\max S(t), \qquad \text{(Equation 19)}$$

$$\psi_l(t)=\max \psi(t), \qquad \text{(Equation 20),}$$

wherein $S(t)=[S_1(t), \ldots, S_m-1(t), S_m(t)]$ is the vector of activity degree of hidden neurons at time t, $\psi(t)=[\psi_1(t), \ldots, \psi_m-1(t), \psi_m(t)]$ is the vector of independent contribution of hidden neurons at time t, the hidden neuron is added and the number of hidden neurons is updated using $M_1=m+1$ or the structure of self-organizing recurrent RBF neural network is not adjusted, $M_1=m$, when the activity degree and independent contribution of the ith hidden neuron satisfy:

$$S_i(t)=\min S(t), \qquad \text{(Equation 21)}$$

$$\psi_i(t)=\min \psi(t), \qquad \text{(Equation 22)}$$

wherein the ith hidden neuron is deleted and the number of the hidden neurons is updated using $M_2=M_1-1$ or the structure of self-organizing recurrent RBF neural network is not adjusted, $M_2=M_1$;

(7) increasing a learning steps:

if s<N, turning to step (3)

if s=N, turning to step (8); and (8) calculating the performance of self-organizing recurrent RBF neural network according to Equation 5:

if E(t)≥Ed, then turning to step (3); and if $E(t)<E_d$, stopping the training process; and (4) inputting into the trained self-organizing RBF neural network values of the input variables associated with at least one testing sample associated with the sewage treatment process of the activated sludge system and computing the output value of the trained self-organizing RBF neural network into which the values of the input variables were entered as the BOD concentration associated with the at least one testing sample, wherein the sewage treatment process is controlled based on the BOD concentration associated with the at least one testing sample.

* * * * *